(12) United States Patent
Shimoyama et al.

(10) Patent No.: US 9,439,742 B2
(45) Date of Patent: *Sep. 13, 2016

(54) ELECTRIC TOOTHBRUSH

(71) Applicant: OMRON HEALTHCARE Co., Ltd., Kyoto-shi, Kyoto (JP)

(72) Inventors: Jun Shimoyama, Uji (JP); Yasutaka Murase, Kyoto (JP); Tadashi Tone, Kyoto (JP); Yuji Asada, Uji (JP)

(73) Assignee: OMRON HEALTHCARE Co., Ltd., Muko-shi (JP)

( * ) Notice: Subject to any disclaimer, the term of this patent is extended or adjusted under 35 U.S.C. 154(b) by 70 days.

This patent is subject to a terminal disclaimer.

(21) Appl. No.: 14/315,113

(22) Filed: Jun. 25, 2014

(65) Prior Publication Data

US 2014/0366289 A1 Dec. 18, 2014

Related U.S. Application Data

(63) Continuation of application No. 12/377,355, filed as application No. PCT/JP2007/063680 on Jul. 9, 2007, now Pat. No. 8,793,829.

(30) Foreign Application Priority Data

Aug. 29, 2006 (JP) ................................ 2006-232528
Feb. 27, 2007 (JP) ................................ 2007-047831

(51) Int. Cl.
*A61C 17/22* (2006.01)
*A61C 17/34* (2006.01)
*A46B 13/02* (2006.01)

(52) U.S. Cl.
CPC ......... *A61C 17/3481* (2013.01); *A46B 13/023* (2013.01)

(58) Field of Classification Search
CPC .. A61C 17/3481; A61C 17/34; A61C 17/32; A46B 13/023; A46B 13/02; A46B 13/008; A46B 13/00
USPC ............................................ 15/22.1; 433/118
See application file for complete search history.

(56) References Cited

U.S. PATENT DOCUMENTS 4,175,299 A 11/1979 Teague, Jr. et al.
4,249,896 A * 2/1981 Kerfoot, Jr. .............. A61C 1/05
433/126

(Continued)

FOREIGN PATENT DOCUMENTS

DE 555 481 7/1932
DE 299 13 406 12/1999

(Continued)

OTHER PUBLICATIONS

Shimoyama, J. et al., U.S. Office Action mailed Dec. 20, 2012, directed to U.S. Appl. No. 12/377,355; 17 pages.

(Continued)

*Primary Examiner* — Tatiana Nobrega
(74) *Attorney, Agent, or Firm* — Morrison & Foerster LLP

(57) ABSTRACT

An electric toothbrush includes an inner case, made up of an inner case main body and a motor holder, mounted with various components including a motor; an outer case which interiorly accommodates the inner case and which acts as a portion the user grips with hand when brushing teeth; an eccentric shaft, configured by a shaft main body and an eccentric member, which center of gravity is arranged at a position shifted from a shaft center and which rotates by a drive force of the motor; and a vibration transmitting component for transmitting the vibration generated with the rotation of the eccentric shaft to a brush portion; where the vibration transmitting component is positioned with respect to the outer case by point contacting the inner wall surface of the outer case at a plurality of locations.

7 Claims, 11 Drawing Sheets

(56) References Cited

U.S. PATENT DOCUMENTS

| | | | |
|---|---|---|---|
| 4,336,622 A | 6/1982 | Teague, Jr. et al. | |
| 4,756,202 A | 7/1988 | Kawamoto | |
| 5,911,577 A * | 6/1999 | Henrikson | A61C 17/005 433/125 |
| 5,987,681 A * | 11/1999 | Hahn | A61C 17/3481 15/22.1 |
| 6,421,865 B1 * | 7/2002 | McDougall | A61C 17/22 15/22.1 |
| 6,421,866 B1 * | 7/2002 | McDougall | A61C 17/3481 15/21.1 |
| 6,766,548 B1 | 7/2004 | Lukas et al. | |
| 6,829,801 B2 | 12/2004 | Schütz | |
| 6,851,150 B2 | 2/2005 | Chiang | |
| 7,024,718 B2 | 4/2006 | Chu | |
| 7,156,108 B2 | 1/2007 | Xin | |
| 7,386,904 B2 | 6/2008 | Fattori | |
| 7,690,067 B2 | 4/2010 | Schaefer et al. | |
| 8,089,227 B2 | 1/2012 | Baertschi et al. | |
| 8,499,851 B2 * | 8/2013 | Hata | B06B 1/16 15/22.1 |
| 8,510,890 B2 * | 8/2013 | Hoshino | A61C 17/3481 15/22.1 |
| 8,522,797 B2 * | 9/2013 | Dickie | A61C 15/047 132/309 |
| 2002/0120991 A1 * | 9/2002 | Cacka | A61C 17/225 15/22.1 |
| 2004/0010872 A1 * | 1/2004 | Chiang | A61C 17/34 15/28 |
| 2004/0060136 A1 | 4/2004 | Gatzemeyer et al. | |
| 2004/0177458 A1 | 9/2004 | Chan et al. | |
| 2005/0150067 A1 | 7/2005 | Cobabe et al. | |
| 2005/0189000 A1 | 9/2005 | Cacka et al. | |
| 2006/0010622 A1 | 1/2006 | Naruse et al. | |
| 2006/0168745 A1 | 8/2006 | Kobayashi et al. | |
| 2006/0210948 A1 * | 9/2006 | Rose | A61C 17/005 433/125 |
| 2006/0254007 A1 | 11/2006 | Banning | |
| 2009/0064429 A1 | 3/2009 | Hall et al. | |
| 2009/0320221 A1 | 12/2009 | Masuko | |

FOREIGN PATENT DOCUMENTS

| | | |
|---|---|---|
| JP | 6-34796 | 5/1994 |
| JP | 10-192054 | 7/1998 |
| JP | 2003-164473 | 6/2003 |
| JP | 2005-131342 | 5/2005 |

OTHER PUBLICATIONS

Shimoyama, J. et al. U.S. Office Action mailed Jun. 6, 2013, directed to U.S. Appl. No. 12/377,355; 10 pages.

Shimoyama, J. et al. U.S. Office Action mailed Sep. 25, 2013, directed to U.S. Appl. No. 12/377,355; 9 pages.

Shimoyama, J. et al. U.S. Notice of Allowance mailed Apr. 16, 2014, directed to U.S. Appl. No. 12/377,355; 9 pages.

Office Action issued on Jul. 30, 2014, directed to DE Application No. 11 2007 002 038.5; 4 pages.

* cited by examiner

ELECTRIC TOOTHBRUSH

CROSS REFERENCE TO RELATED APPLICATIONS

This application is a continuation of U.S. patent application Ser. No. 12/377,355, filed Jul. 9, 2007, which is a National Phase filing under 35 U.S.C. §371 of International Application No. PCT/JP2007/063680, filed Jul. 9, 2007, which claims priority to Japanese Application Nos. 2006-232528, filed Aug. 29, 2006, and 2007-047831, filed Feb. 27, 2007, the entire contents of which are hereby incorporated by reference.

FIELD OF THE INVENTION

The present invention relates to an electric toothbrush.

BACKGROUND OF THE INVENTION

An electric toothbrush internally equipped with a vibration source and configured to transmit the vibration from the vibration source to a brush portion is conventionally known. In such an electric toothbrush, the brush portion needs to be sufficiently vibrated to exhibit an effect of brushing teeth and to enable a user himself/herself to sufficiently have actual feeling of brushing teeth. If the vibration of the portion the user grips is too large when brushing teeth, the user sometimes feels unpleasant, and thus it is desirable that the relevant portion does not vibrate too much.

In order to sufficiently vibrate the brush portion and to not vibrate the portion the user grips with hand as much, consideration is made in arranging a vibration proof member for absorbing the vibration near the end on the opposite side of a component at which distal end the brush portion is arranged. However, this is not desirable in terms of energy efficiency since absorbing the vibration with the vibration proof member leads to losing some of the vibration energy generated by the vibration source.

Therefore, suppressing the vibration of the portion the user grips with hand while sufficiently vibrating the brush portion and suppressing the loss of vibration energy involve technical difficulty.

A technique of vibrating the brush portion by arranging an eccentric shaft bearing near the brush portion is known (Patent Document 3). However, such a technique has problems such as increase in slidable movement resistance and increase in an operation sound and vibration.

The related technique includes those disclosed in Patent Documents 1, 2, and 3.
[Patent Document 1] Japanese Examined Patent Publication No. 6-34796
[Patent Document 2] Japanese Unexamined Patent Publication No. 8-117258
[Patent Document 3] Japanese Unexamined Patent Publication No. 10-192054

SUMMARY OF THE INVENTION

It is an object of the present invention to provide an electric toothbrush capable of suppressing loss of vibration energy while suppressing vibration of the portion a user grips with hand.

The present invention adopts the following means to solve the above problems.

An electric toothbrush of the present invention relates to an electric toothbrush including an inner case which is mounted with various components including a drive source; an outer case which interiorly accommodates the inner case, and which becomes a portion a user grips with hand when brushing teeth; an eccentric shaft which center of gravity is arranged at a position shifted from a shaft center and which rotates by a drive force of the drive source; and a vibration transmitting component which transmits a vibration generated with the rotation of the eccentric shaft to a brush portion; wherein the vibration transmitting component is positioned with respect to the outer case by point contacting an inner wall surface of the outer case at a plurality of locations.

When point contacting the members, it is physically impossible to contact at a perfect point, and contact is made, in reality, at a surface of a very small area. Therefore, "point contact" in the present invention includes area contact of a very small area.

According to the present invention, the vibration transmitting component is positioned with respect to the outer case by point contacting the inner wall surface of the outer case at a plurality of locations. Thus, transmission of the vibration of the vibration transmitting component to the outer case can be suppressed. Therefore, the outer case, which becomes the portion the user grips with hand when brushing teeth, is suppressed from vibrating.

The movement of the vibration transmitting component is not greatly limited by the outer case. Therefore, the vibration transmitting component can be freely vibrated without being greatly restricted by the outer case. Accordingly, the loss of vibration energy can be suppressed.

Furthermore, the vibration transmitting component may include a stem, made from a hard material, arranged with an eccentric shaft bearing; a holder, made from a hard material, arranged so as not to contact the stem and fixed to the inner case; and an elastic member having an interposing portion interposed so as to be sandwiched between the stem and the holder, and a plurality of projecting portions that point contacts the inner wall surface of the outer case.

According to such a configuration, the vibration transmitting component is elastically point contacted to the inner wall surface of the outer case. Therefore, the movement of the vibration transmitting component is more reliably prevented from being limited by the outer case. Furthermore, the vibration of the stem is suppressed from being transmitted to the holder since the interposing portion of the elastic member is interposed between the stem and the holder. Thus, the vibration of the stem is suppressed from being transmitted to the inner case through the holder.

The vibration transmitting component can be more reliably fixed to the inner case since the holder to be fixed to the inner case is made from a hard material. Moreover, the original function of the vibration transmitting component of transmitting the vibration generated with the rotation of the eccentric shaft to the brush portion is sufficiently exhibited since the stem arranged with the eccentric shaft bearing is made from a hard material.

Preferably, the elastic member is a molded article having elastomer as a raw material; and the vibration transmitting component is integrally molded by insert molding with the stem and the holder as insert parts.

In this manner, the vibration transmitting component can be handled as one component. The sealability between the stem and the elastic member, and between the elastic member and the holder can be sufficiently exhibited.

Furthermore, a rotation-preventing structure may be arranged between the stem and the elastic member, and between the elastic member and the holder.

Therefore, the members are prevented from shifting in a rotating direction.

The vibration transmitting component suitably includes a stem, made from a hard material, arranged with the eccentric shaft bearing; and a holder, made from an elastic material, fixed to the inner case and having a plurality of projecting portions that point contact the inner wall surface of the outer case.

When adopting such a configuration as well, the vibration transmitting component elastically point contacts the inner wall surface of the outer case. Therefore, the movement of the vibration transmitting component is more reliably prevented from being limited by the outer case. The vibration of the stem is suppressed from being transmitted to the inner case. Furthermore, the original function of the vibration transmitting component of transmitting the vibration generated with the rotation of the eccentric shaft to the brush portion is sufficiently exhibited since the stem arranged with the eccentric shaft bearing is made from a hard material.

A seal ring for sealing a clearance between the outer case and the vibration transmitting component is preferably arranged.

Therefore, water and the like are prevented from entering inside from between the outer case and the vibration transmitting component.

A space region for storing a lubricant to supply to a slidably moving portion of the eccentric shaft and the bearing is preferably arranged at a distal end portion in an interior of the stem.

Thus, the lubricant can be interposed over a long period of time at the slidably moving portion of the eccentric shaft and the bearing by storing the lubricant in the space region. Thus, the slidably moving state of the eccentric shaft and the bearing can be stabilized over a long period of time. Therefore, the vibration state of each portion can be stabilized over a long period of time. Moreover, increase in the slidable movement resistance can be suppressed, generation of abnormal noise can be suppressed, and increase in vibration can be suppressed.

Preferably, the space region is positioned on a distal end side than the bearing; and the distal end of the eccentric shaft projects out to the space region side than the bearing.

Therefore, the distal end of the eccentric shaft is in a state of contacting the lubricant, whereby the lubricant can be actively introduced to the slidably moving portion of the eccentric shaft and the bearing.

Moreover, a brush component which includes a tubular portion to be attached to the vibration transmitting component and a brush portion arranged at a distal end of the tubular portion, and which is configured to be removable with respect to the vibration transmitting component is further arranged; wherein with the brush component attached to the vibration transmitting component, a vicinity of one end and a vicinity of the other end of the tubular portion contact the stem, and a clearance is formed between an inner wall surface of the tubular portion and an outer wall surface of the stem at an intermediate portion.

Therefore, the location the vibration is directly transmitted from the vibration transmitting component to the brush component can be a limited portion (i.e., contacting portion). The efficiency of the vibration transmission with respect to the brush portion thus can be enhanced as much as possible, and the transmission of vibration to the portion the user grips with hand when brushing teeth can be suppressed.

The contact between the tubular portion and the stem may be point contact at a plurality of locations with respect to a peripheral direction, or line contact at a plurality of locations with respect to the peripheral direction.

Therefore, the location the vibration is directly transmitted from the vibration transmitting component to the brush component can be a more limited portion.

The "point contact" includes area contact of a very small area in the present invention, as described above. When contacting the members by line contact, it is physically impossible to contact at a perfect line, and contact is made, in reality, at a surface of a very small area. Therefore, "line contact" in the present invention includes area contact of very small area, similar to the point contact.

An electric toothbrush of the present invention relates to an electric toothbrush including an eccentric shaft which center of gravity is arranged at a position shifted from a shaft center; and a vibration transmitting component which transmits vibration generated with the rotation of the eccentric shaft to a brush portion; wherein the vibration transmitting component includes a stem arranged with an eccentric shaft bearing; and a space region for storing a lubricant to supply to a slidably moving portion of the eccentric shaft and the bearing is arranged at a distal end portion in an interior of the stem.

According to the present invention, the lubricant can be interposed over a long period of time at the slidably moving portion of the eccentric shaft and the bearing by storing the lubricant in the space region. Thus, the slidably moving state of the eccentric shaft and the bearing can be stabilized over a long period of time. Therefore, the vibration state of each portion can be stabilized over a long period of time. Moreover, increase in the slidable movement resistance can be suppressed, generation of abnormal noise can be suppressed, and increase in vibration can be suppressed.

Preferably, the space region is positioned on a distal end side than the bearing; and the distal end of the eccentric shaft projects out to the space region side than the bearing.

The distal end of the eccentric shaft is thus in a state of contacting the lubricant. Therefore, the lubricant can be actively introduced to the slidably moving portion of the eccentric shaft and the bearing.

An electric toothbrush of the present invention relates to an electric toothbrush including an eccentric shaft which center of gravity is arranged at a position shifted from a shaft center; a vibration transmitting component which transmits vibration generated with the rotation of the eccentric shaft to a brush portion; and a brush component which includes a tubular portion to be attached to the vibration transmitting component and a brush portion arranged at a distal end of the tubular portion, and which is configured to be removable with respect to the vibration transmitting component; wherein the vibration transmitting component includes a stem arranged with the eccentric shaft bearing; and with the brush component attached to the vibration transmitting component, a vicinity of one end and a vicinity of the other end of the tubular portion contact the stem, and a clearance is formed between an inner wall surface of the tubular portion and an outer wall surface of the stem at an intermediate portion.

According to the present invention, the location the vibration is directly transmitted from the vibration transmitting component to the brush component can be a limited portion (i.e., contacting portion). Therefore, the efficiency of the vibration transmission with respect to the brush portion can be enhanced as much as possible, and the transmission of vibration to the portion the user grips with hand when brushing teeth can be suppressed.

The contact between the tubular portion and the stem may be point contact at the plurality of locations with respect to a peripheral direction, or line contact at the plurality of locations with respect to the peripheral direction.

Therefore, the location the vibration is directly transmitted from the vibration transmitting component to the brush component can be a more limited portion.

The eccentric shaft is preferably configured by a shaft main body and an eccentric member arranged on the brush portion side than the shaft main body; and the shaft main body includes a first shaft member connected to the eccentric member, and a second shaft member connected to a side opposite to the eccentric member with respect to the first shaft member, and having higher flexibility than the first shaft member.

The vibration generated by the eccentric member is thus absorbed by the second shaft member. Therefore, the transmission of vibration to the portion the user grips with hand when brushing teeth can be further suppressed.

A central portion of the second shaft member preferably includes a small diameter portion, which outer diameter is smaller than an outer diameter of the first shaft member.

Therefore, the transmission of vibration from the eccentric member side to the portion side the user grips with hand when brushing teeth can be further suppressed.

Each of the above configuration may be combined as much as possible for use.

According to the present invention, the suppression in the loss of vibration energy can be achieved while suppressing the vibration of the portion the user grips with hand, as described above.

DESCRIPTION OF THE REFERENCE SYMBOLS

Figure 1:
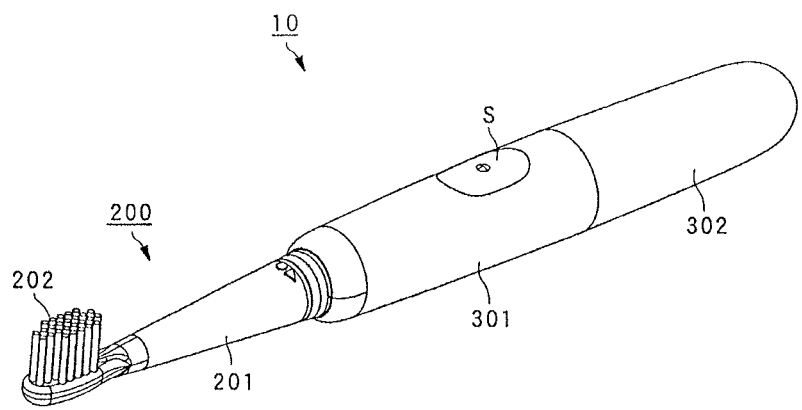
FIG. 1 is a perspective view of an outer appearance of an electric toothbrush according to a first embodiment of the present invention.

10 Electric toothbrush
100, 100a, 100b Vibration transmitting component
110 Stem
111 Fixing portion
112 Projection
113 Fit-in projection
115 Space region
120 Holder
121 Pass-through hole
122 Pass-through hole
130 Elastic member
131 Projecting portion
132 Interposing portion
140 Holder
141 Projecting portion
142 Pass-through hole
150 Stem portion
151 Fixing portion
152 Projecting portion
153 Pass-through hole
200 Brush component
201 Tubular portion
201a Plane portion
202 Brush portion
203 Groove
301 Outer case
301a Male screw
302 Cap
302a Female screw
303 Inner case main body
303a Switch
304 Motor holder
304a Lock projection
305 Motor
306 Shaft main body
307 Eccentric member
307a Distal end (of eccentric shaft)
308 First shaft member
309 Second shaft member 309a First fit-in portion
309b Second fit-in portion
309c Small diameter portion
400 Bearing
B Machine screw
C Clearance
D Battery
F Vicinity of front end
O Lubricant oil
R Vicinity of rear end
S Switch button
S1 Seal ring
S2 Seal ring
X Slidably moving portion Best modes for carrying out the present invention will now be illustratively described in detail below based on embodiments with reference to the drawings. The dimension, material, shape, relative arrangement, and the like of components described in the embodiments are not intended to limit the scope of the present invention unless specific description is particularly made.

An electric toothbrush according to a first embodiment of the present invention will be described with reference to FIGS. 1 to 10.

Figure 2:
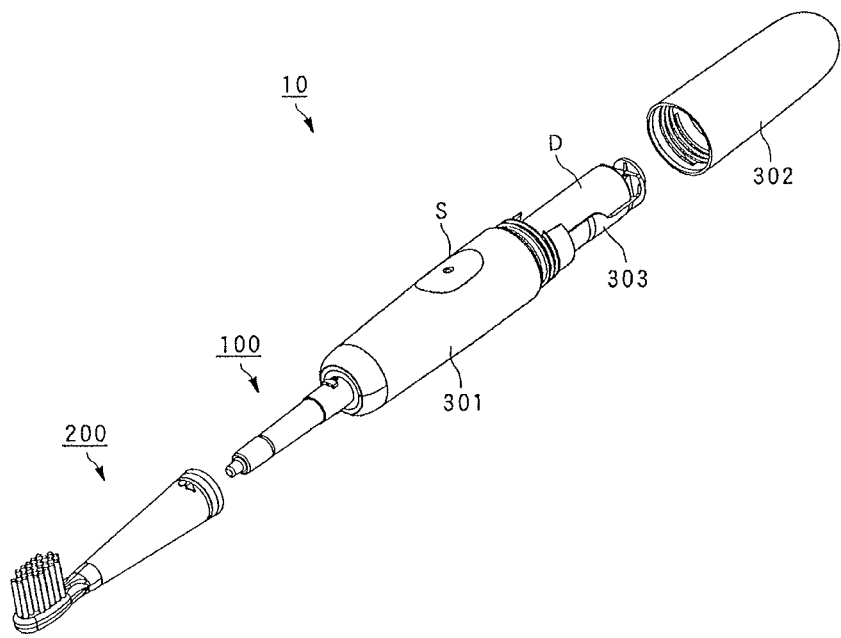
FIG. 2 is a perspective view showing a state in which a cap and a brush component are detached in the electric toothbrush according to the first embodiment of the present invention.

The schematic configuration of the electric toothbrush according to the first embodiment of the present invention will be described with reference to FIGS. 1 and 2. FIG. 1 is a perspective view of an outer appearance of the electric toothbrush according to the first embodiment of the present invention. FIG. 2 is a perspective view showing a state in which a cap and a brush component are detached in the electric toothbrush according to the first embodiment of the present invention.

An electric toothbrush 10 according to the present embodiment includes an outer case 301 serving as a portion the user grips with hand when brushing teeth, a brush component 200 arranged on the distal end side of the outer case 301, and a cap 302 arranged on the rear end side of the outer case 301.

The outer case 301 is configured by a tubular member, where an inner case mounted with various components is accommodated therein. The outer case 301 is arranged with a switch button S for switching the power to ON or OFF.

A vibration transmitting component 100 for transmitting the vibration to the brush component 200 is arranged so as to project out from the inside to the outside of the outer case 301 from the distal end side of the outer case 301. The brush component 200 is attached to the vibration transmitting component 100 so as to cover the vibration transmitting component 100.

The brush component 200 includes a tubular portion 201 to be attached to the vibration transmitting component 100, and a brush portion 202 arranged at the distal end of the tubular portion 201. The brush component 200 is a consumable part, and is configured to be removable with respect to the vibration transmitting component 100 so as to be appropriately changed with a new one.

One part of an inner case main body 303 configuring the inner case is arranged to project out from the inside to the outside of the outer case 301 from the rear end side of the outer case 301. Therefore, one part of the inner case main body 303 is opened by detaching the cap 302 thereby enabling a battery D to be changed.

Figure 3:
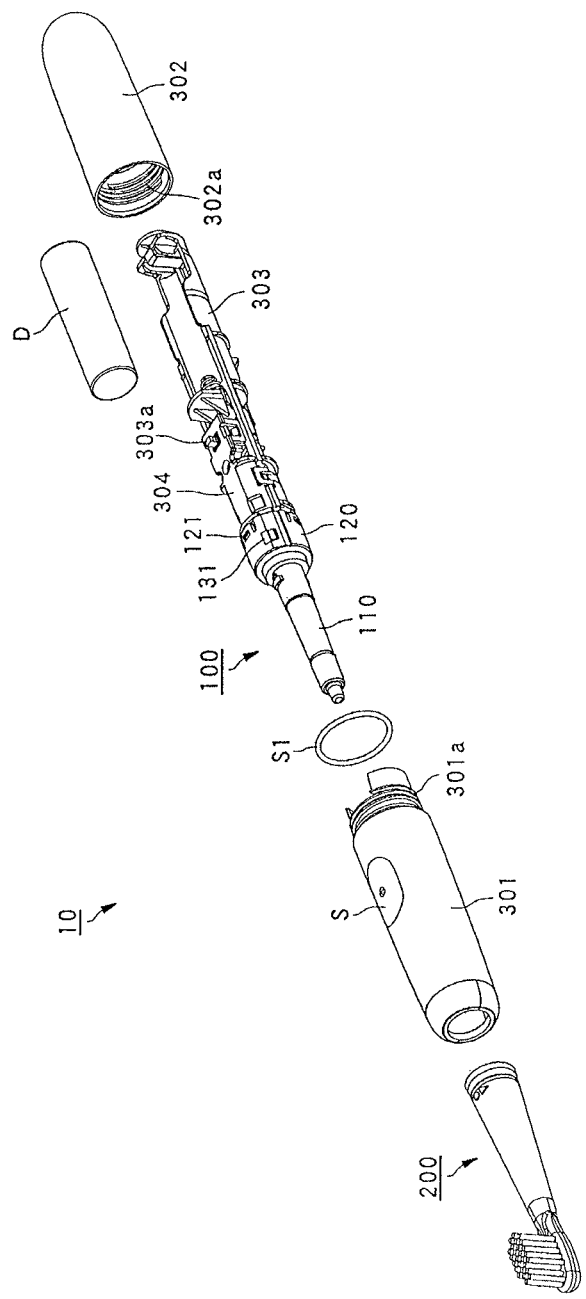
FIG. 3 is an exploded perspective view of the electric toothbrush according to the first embodiment of the present invention.
Figure 4:
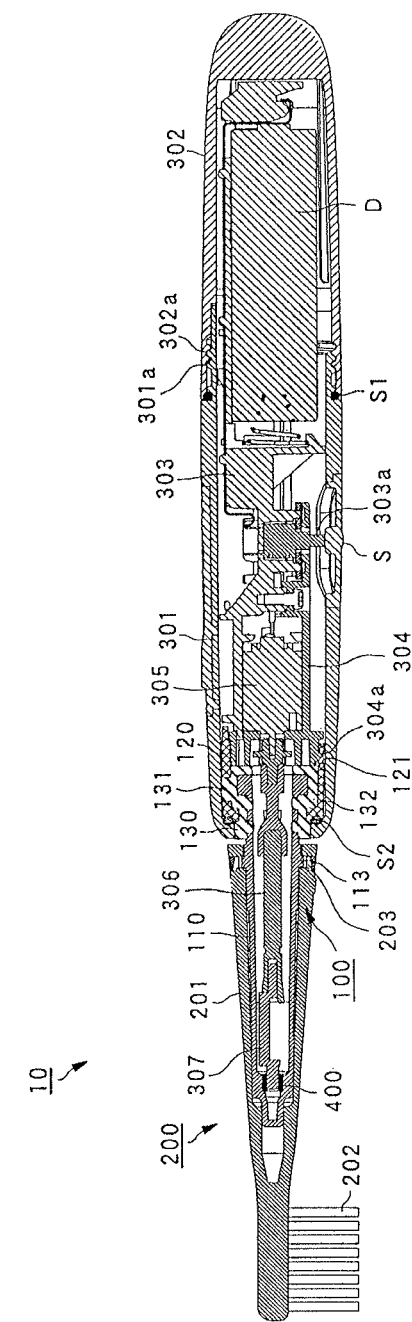
FIG. 4 is a cross-sectional view of the electric toothbrush according to the first embodiment of the present invention.
Figure 5:
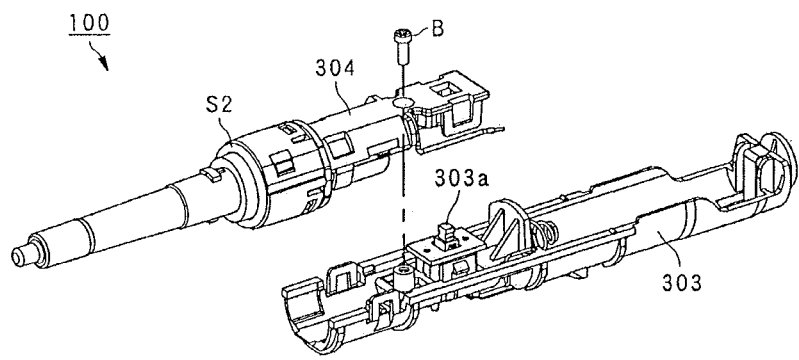
FIG. 5 is a perspective view showing a fixed structure of an inner case and a vibration transmitting component in the electric toothbrush according to the first embodiment of the present invention.
Figure 6:
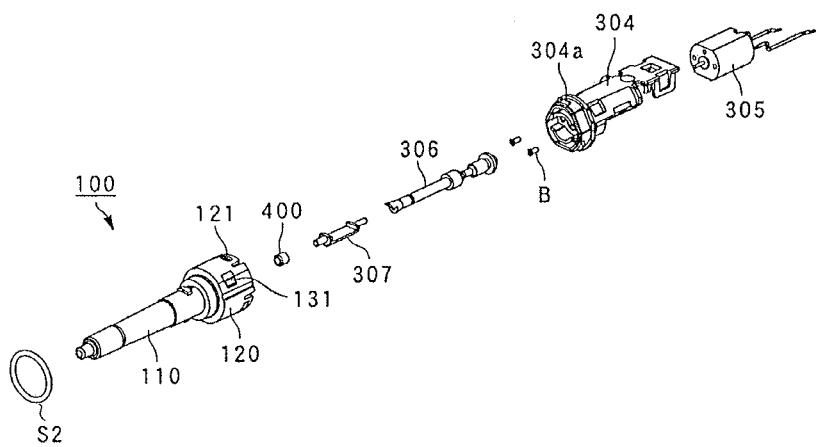
FIG. 6 is a perspective view further exploded for the vibration transmitting component and some components mounted on the inner case in the electric toothbrush according to the first embodiment of the present invention.

The internal configuration of the electric toothbrush 10 according to the first embodiment of the present invention will be described with particular reference to FIGS. 3 to 6. FIG. 3 is an exploded perspective view of the electric toothbrush according to the first embodiment of the present invention. FIG. 4 is a cross-sectional view of the electric toothbrush according to the first embodiment of the present invention. FIG. 4 is a cross-sectional view (cross-sectional view in longitudinal direction) cut so as to pass through a center axis of the electric toothbrush. FIG. 5 is a perspective view showing a fixed structure of the inner case and the vibration transmitting component in the electric toothbrush according to the first embodiment of the present invention. FIG. 6 is a perspective view further exploded for the vibration transmitting component and some components mounted on the inner case in the electric toothbrush according to the first embodiment of the present invention.

The inner case including the inner case main body 303 and a motor holder 304 is accommodated inside the outer case 301. The inner case is mounted with a motor 305 serving as a drive source, and the battery D serving as a power supply for supplying electricity to the motor 305.

The inner case main body 303 is arranged with a switch 303a for switching the power to ON or OFF. The switch 303a arranged on the inner case main body 303 is pushed when the switch button S arranged on the outer case 301 is pushed.

The motor 305 is fixed to the motor holder 304 by a machine screw B, and such a motor holder 304 is fixed to the inner case main body 303 by the machine screw B as shown in FIG. 5. An eccentric shaft configured by a shaft main body 306 and an eccentric member 307 is coaxially fixed with respect to the shaft of the motor 305 fixed to the motor holder 304.

The distal end of the eccentric shaft (more specifically, distal end of eccentric member 307) is supported in a freely rotating state by a bearing 400 arranged inside the vibration transmitting component 100. A very small clearance is formed between the eccentric shaft and the bearing 400.

The motor holder 304 has a plurality of lock projections 304a. A plurality of pass-through holes 121 to which the lock projections 304a lock are formed in the vibration transmitting component 100. The plurality of lock projections 304a are locked to the plurality of pass-through holes 121 so that the vibration transmitting component 100 is fixed to the motor holder 304 configuring the inner case.

The vibration transmitting component 100 is fixed to the inner case including the inner case main body 303 and the motor holder 304 in such a manner (see FIG. 3). With the vibration transmitting component 100 fixed to the inner case, the vibration transmitting component 100 fixed to the inner case is inserted from an opening on the rear end side of the outer case 301, and the vibration component 100 and the inner case are attached to the outer case 301 such that the vibration transmitting component 100 projects out from an opening on the distal end side of the outer case 301.

A seal ring S2 is attached to the vibration transmitting component 100. When the vibration transmitting component 100 is attached to the outer case 301, the seal ring S2 closely attaches to the inner peripheral surface near the open end of the outer case 301. The gap between the outer case 301 and the vibration transmitting component 100 is thus sealed, thereby preventing water and the like from entering from between.

A male screw 301a is provided on the outer peripheral surface of the rear end of the outer case 301, and a female screw 302a is provided at the inner periphery of the open end of the cap 302. The cap 302 is fixed to the outer case 301 by screw-fitting the male screw 301a and the female screw 302a.

A seal ring S1 is attached to a region corresponding to the distal end of the cap 302 at the outer peripheral surface of the outer case 301. The distal end of the cap 302 thus closely attaches to the seal ring S1 when the cap 302 is fixed to the outer case 301. The gap between the outer case 301 and the cap 302 is thus sealed, thereby preventing water and the like from entering inside from between.

Figure 7:
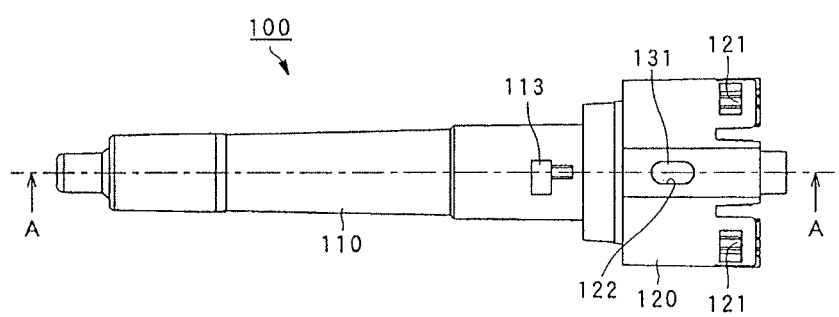
FIG. 7 is a plan view of the vibration transmitting component according to the first embodiment of the present invention.
Figure 8:
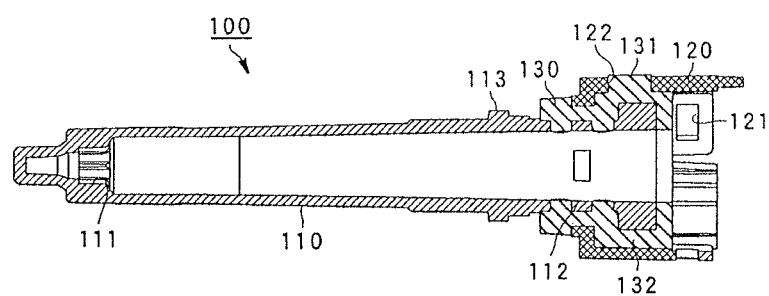
FIG. 8 is a cross-sectional view of the vibration transmitting component according to the first embodiment of the present invention.
Figure 9:
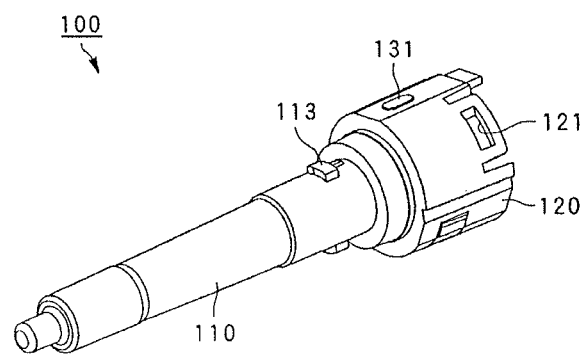
FIG. 9 is a perspective view of the vibration transmitting component according to the first embodiment of the present invention seen from the distal end side.
Figure 10:
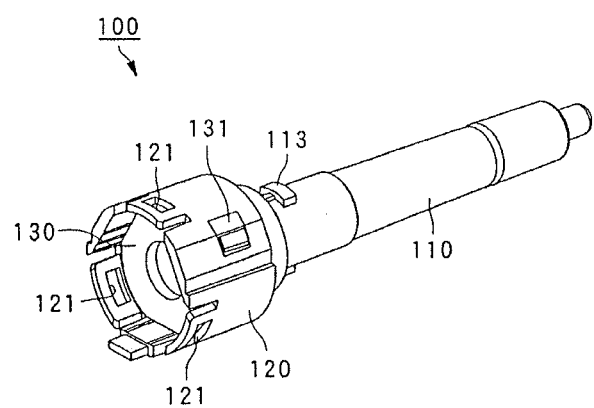
FIG. 10 is a perspective view of the vibration transmitting component according to the first embodiment of the present invention seen from the rear end side.

The vibration transmitting component 100 according to the first embodiment of the present invention will be more specifically described with particular reference to FIGS. 7 to 10. FIG. 7 is a plan view of the vibration transmitting component according to the first embodiment of the present invention. FIG. 8 is a cross-sectional view of the vibration transmitting component according to the first embodiment of the present invention. FIG. 8 is a cross-sectional view taken along AA of FIG. 7. FIG. 9 is a perspective view of the vibration transmitting component according to the first embodiment of the present invention seen from the distal end side. FIG. 10 is a perspective view of the vibration transmitting component according to the first embodiment of the present invention seen from the rear end side.

The vibration transmitting component 100 according to the present embodiment is configured by a stem 110 made from a hard material (e.g., resin material), a holder 120 made from a hard material (e.g., resin material) arranged so as not to contact the stem 110, and an elastic member 130 using elastomer as a raw material.

In the vibration transmitting component 100 according to the present embodiment, the elastic member 130 is a molded article molded by a die. That is, the vibration transmitting component 100 is obtained by integrally molding the elastic member 130 by insert molding with the stem 110 and the holder 120 as insert parts.

The stem 110 is a tubular member having a closed distal end, where a fixing portion 111 for fixing the bearing 400 is arranged at the distal end in the interior of the tube. A plurality of projections 112 are arranged on the outer wall surface near the open end of the stem 110. The elastic member 130 is prevented from shifting in the rotating direction by such projections 112.

A fit-in projection 113 for fixing the brush component 200 is also arranged on the outer wall surface of the stem 110. The inner wall surface of the tubular portion 201 in the brush component 200 is formed with an L-shaped groove 203 (see FIG. 4) so as to be fitted with the fit-in projection 113.

According to such a configuration, the brush component 200 can be fixed to the stem 110 by axially fitting and then slightly rotating the tubular portion 201 so that the fit-in projection 113 lies along the groove 203 of the tubular portion 201.

The holder 120 is a tubular member having an inner diameter larger than the outer diameter of the stem 110. A plurality of pass-through holes 121 to which the plurality of lock projections 304a arranged on the motor holder 304 lock, as described above, is formed near the rear end of the holder 120.

The elastic member 130 includes an interposing portion 132 interposed so as to be sandwiched between the stem 110 and the holder 120, and a plurality of (three in the present embodiment) projecting portions 131 arranged so as to project out from a plurality of pass-through holes 122 formed in the holder 120.

The shape in the direction perpendicular to the axis at the closely-attached portion of the interposing portion 132 in the elastic member 130 and the holder 120 is noncircular. In the present embodiment, a shape cut with a straight line at three locations is realized with respect to a circle (see FIG. 10).

Thus, the elastic member 130 is prevented from shifting in the rotating direction with respect to the holder 120.

When the vibration transmitting component 100 configured as above is attached in the outer case 301, only the plurality of projecting portions 131 arranged on the elastic member 130 of the vibration transmitting component 100 contact the inner wall surface of the outer case 301 by point contact (area contact of very small area). Therefore, the vibration transmitting component 100 is positioned only by point contact at a plurality of locations with respect to the outer case 301. In the present embodiment, three projecting portions 131 are arranged, as described above, and positioning is carried out by three point contacts.

An operation of the electric toothbrush 10 configured as above will now be described. When the power is turned ON by the switch button S, the shaft of the motor 305 rotates, and the eccentric shaft (configured by the shaft main body 306 and the eccentric member 307) fixed to the relevant shaft rotates. The eccentric member 307 is arranged at a position its center of gravity is shifted from the shaft center.

Therefore, if the eccentric shaft is rotated without the distal end of the eccentric shaft supported by the bearing 400, the eccentric member 307 moves so as to turn about the shaft center while rotating. Thus, if the eccentric shaft is rotated with the eccentric shaft supported by the bearing 400, an operation is performed in which the outer wall surface near the distal end of the eccentric shaft repeatedly hits the inner wall surface of the bearing 400 for a great number of times in a short period of time.

According to such an operation, the stem 110 fixed with the bearing 400 can be vibrated through the bearing 400. When the stem 110 vibrates, such vibration can be transmitted to the brush component 200 fixed to the stem 110. Therefore, the brush portion 202 vibrates by the vibration of the brush component 200, and the teeth can be brushed by placing the brush portion 202 on the teeth.

Therefore, according to the electric toothbrush 10 of the present embodiment, the vibration transmitting component 100 is configured to be positioned with respect to the outer case 301 by point contacting the inner wall surface of the outer case 301 at the plurality of locations (three locations in the present embodiment).

Therefore, the vibration of the vibration transmitting component 100 is suppressed from being transmitted to the outer case 301. Thus, the outer case 301, which is the portion the user grips with hand when brushing teeth, is suppressed from vibrating. The user is then suppressed from feeling unpleasant when brushing teeth.

Since the vibration transmitting component 100 is simply positioned by point contact at the plurality of locations with respect to the outer case 301, the movement of the vibration transmitting component 100 is barely limited by the outer case 301. Thus, the vibration transmitting component 100 can be freely vibrated without barely being restricted by the outer case 301. Accordingly, the loss of vibration energy can be suppressed. Therefore, the vibration transmitting component 100 as well as the brush component 200 fixed thereto can be greatly vibrated with small power and with satisfactory efficiency.

Furthermore, in the present embodiment, the vibration transmitting component 100 is configured by the stem 110 made from a hard material, the holder 120 made from the same hard material, and the elastic member 130 made from elastomer, as described above.

The plurality of projecting portions 131 arranged on the elastic member 130 point contact the inner wall surface of the outer case 301. Therefore, the vibration transmitting component 100 elastically point contacts the inner wall surface of the outer case 301. Thus, the movement of the vibration transmitting component 100 is more reliably prevented from being limited by the outer case 301.

The vibration of the stem 110 is suppressed from being transmitted to the holder 120 since the interposing portion 132 of the elastic member 130 is interposed between the stem 110 and the holder 120. Therefore, the vibration of the stem 110 is transmitted to the inner case through the holder 120 (more specifically, from the holder 120 to the inner case main body 303 through the motor holder 304), and such vibration is suppressed from being further transmitted to the outer case 301.

One reason the vibration of the stem 110 is suppressed from being transmitted to the holder 120 by interposing the interposing portion 132 between the stem 110 and the holder 120 is that the vibration energy is absorbed by the elastic member 130. However, the present embodiment has features in the configuration in which the vibration transmitting component 100 can vibrate freely as much as possible while supporting the vibration transmitting component 100 with the outer case 301 and the inner case.

In other words, a configuration of preventing the vibration from being transmitted to the outer case 301 by freely vibrating the vibration transmitting component 100 as much as possible is adopted instead of preventing the vibration from being transmitted to the outer case 301 by absorbing the vibration energy. Therefore, the absorption amount of the vibration energy by the interposing portion 132 does not need to be large. Therefore, the absorption amount of the vibration energy by the interposing portion 132 is set small to an extent that energy loss does not arise as a problem.

Here, the rotational force may apply to the stem 110 since the operation of rotating the brush component 200 is involved when attaching the brush component 200 to the stem 110 (also when detaching), as described above.

However, in the present embodiment, the vibration transmitting component 100 can be more reliably fixed to the inner case since the holder 120 fixed to the inner case is made from a hard material. Therefore, the holder 120 of the vibration transmitting component 100 is suppressed from being detached from the inner case even if the rotational force is applied to the stem 110. More specifically, the lock projection 304*a* arranged on the motor holder 304 is suppressed from being detached from the pass-through hole 121 formed in the holder 120.

Moreover, the original function of the vibration transmitting component of transmitting the vibration generated with the rotation of the eccentric shaft to the brush portion 202 is sufficiently exhibited since the stem 110 arranged with the eccentric shaft bearing 400 is made from a hard material.

In the present embodiment, the elastic member 130 is a molded article having elastomer as a raw material. In other words, the vibration transmitting component 100 is obtained by integrally molding the elastic member 130 by insert molding with the stem 110 and the holder 120 as insert parts.

Therefore, the vibration transmitting component 100 can be handled as one component, and superior handleability and superior assembly workability when assembling the electric toothbrush 10 are obtained. Furthermore, superior sealing property between the stem 110 and the elastic member 130 and between the elastic member 130 and the holder 120 is obtained, and the seal member does not need to be separately attached or the members do not need to be adhered by adhesive.

In the present embodiment, the elastic member 130 is prevented from shifting in the rotating direction with respect to the stem 110 by arranging the plurality of projections 112 on the outer wall surface near the open end of the stem 110, as described above. The elastic member 130 is also prevented from shifting in the rotating direction with respect to the holder 120 by forming the shape in the direction perpendicular to the axis at the closely-attached portion of the holder 120 and the interposing portion 132 in the elastic member 130 to noncircular.

Therefore, in the present embodiment, a rotation-preventing structure is arranged between the stem 110 and the elastic member 130, and between the elastic member 130 and the holder 120.

With the use of such a rotation-preventing structure, the rotational force is sometimes applied to the stem 110 when attaching or detaching the brush component 200 to and from the stem 110, as described above, but each member is prevented from shifting in the rotating direction even in such a case. Therefore, the sealability between the members is suppressed from being impaired.

Figure 11:
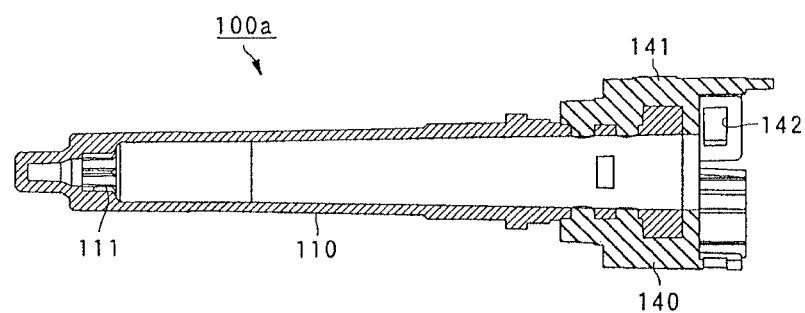
FIG. 11 is a cross-sectional view of a vibration transmitting component according to a second embodiment of the present invention.

FIG. 11 shows a second embodiment of the present invention. A case of configuring the holder with a hard material to more reliably fix the holder and the inner case has been described in the first embodiment.

However, the fixing force of the holder with respect to the inner case does not need to be set as high in some cases such as when configured so that the rotational force does not apply to the stem.

In the present embodiment, an example when configuring the portion of the holder also with elastomer is shown. The configurations and effects other than the vibration transmitting component are the same as the first embodiment, and thus the description thereof will be omitted.

FIG. 11 is a cross-sectional view of a vibration transmitting component according to the second embodiment of the present invention. The cross-section in FIG. 11 shows the cross-section of the same position as FIG. 8 shown in the first embodiment.

A vibration transmitting component 100*a* according to the present embodiment is configured by the stem 110 made from a hard material (e.g., resin material), and a holder 140 having elastomer as a raw material. In the vibration transmitting component 100*a* according to the present embodiment, the holder 140 is a molded article molded by a die. That is, the vibration transmitting component 100*a* is obtained by integrally molding the holder 140 by insert molding with the stem 110 as the insert part.

The configuration of the stem 110 is the same as the first embodiment, and thus the description thereof will be omitted. In the present embodiment, the portion corresponding to the holder 120 in the first embodiment and the portion corresponding to the elastic member 130 are integrated to configure the holder 140. A plurality of projecting portions 141 is arranged on the holder 140. Such projecting portions 141 exhibit the same function as the projecting portion 131 arranged on the elastic member 130 of the first embodiment.

A plurality of pass-through holes 142 is formed near the rear end of the holder 140. The pass-through holes 142 are similar to the case of the first embodiment in being locked by the lock projection 304*a* arranged on the motor holder 304.

Therefore, effects similar to the case of the first embodiment are obtained even when the vibration transmitting component 100*a* according to the present embodiment is adopted other than that the fixing force of the holder with respect to the inner case is inferior to the first embodiment.

Figure 12:
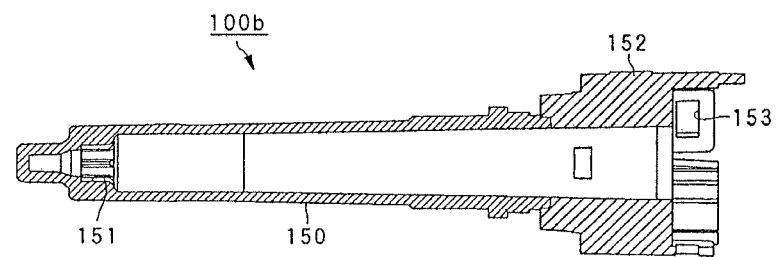
FIG. 12 is a cross-sectional view of a vibration transmitting component according to a third embodiment of the present invention.

FIG. 12 shows a third embodiment of the present invention. In the first and second embodiments, a case of configuring the vibration transmitting component so as to elastically point contact the inner wall surface of the outer case and so as to interpose a member having elastomer as a raw material between the stem and the inner case has been described.

However, the vibration transmitting component can be vibrated freely to a certain extent and transmission of vibration to the outer case can be prevented to a certain extent even if the portion to point contact is hard as long as the vibration transmitting component can be contacted by point contact to the inner wall surface of the outer case. Furthermore, the vibration transmitted to the inner case does not become a large problem in some cases.

Therefore, in the present embodiment, an embodiment of a case in which the vibration transmitting component is configured by a single member made from a hard material is shown. The configurations and effects other than the vibration transmitting component are the same as the first embodiment, and thus the description thereof will be omitted.

FIG. 12 is a cross-sectional view of a vibration transmitting component according to the third embodiment of the present invention. The cross-section in FIG. 12 shows the cross-section of the same position as FIG. 8 shown in the first embodiment.

A vibration transmitting component 100b according to the present embodiment is configured by a single member made from a hard material (e.g., resin material). The vibration transmitting component 100b is integrally configured by a hard material from the portion corresponding to the stem 110, the portion corresponding to the holder 120, and the portion corresponding to the elastic member 130 in the first embodiment.

Therefore, the vibration transmitting component 100b according to the present embodiment also includes a stem portion 150 corresponding to the stem in each embodiment, similar to each embodiment above. A fixing portion 151 for fixing the bearing 400 is arranged at the distal end in the interior of the stem portion 150. A plurality of projecting portions 152 and a plurality of pass-through holes 153 are arranged at the position corresponding to the holder. The projecting portion 152 exhibits functions similar to the projecting portion arranged on the elastic member 130 in the first embodiment. The pass-through hole 153 is locked by the lock projection 304a arranged on the motor holder 304.

Therefore, effects similar to the case of the first embodiment are basically obtained even when adopting the vibration transmitting component 100b according to the present embodiment although the vibration transmission suppressing ability is inferior to the first embodiment. In the case of the present embodiment, the vibration transmitting component 100b is configured by a single member, and thus an advantage in that the configuration is more simplified than the first embodiment is obtained.

Figure 13:
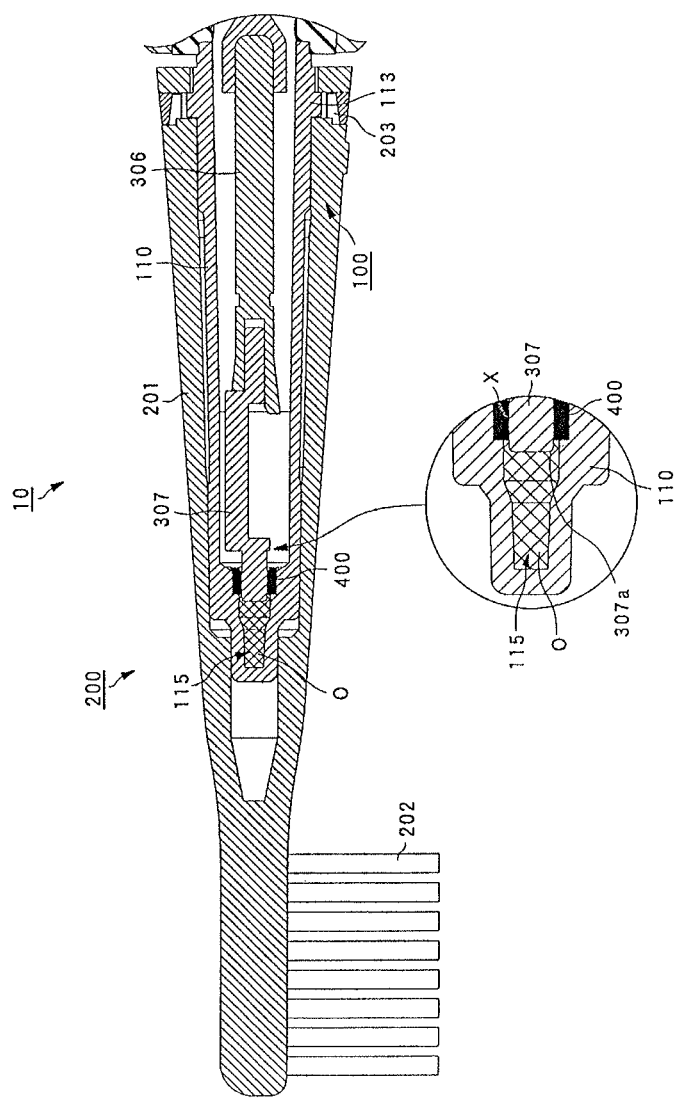
FIG. 13 is one part of a schematic cross-sectional view of an electric toothbrush according to a fourth embodiment of the present invention.

FIG. 13 shows a fourth embodiment of the present invention. In the present embodiment, an embodiment of using a space region formed at the distal end of the eccentric shaft as an oil reservoir for storing lubricant oil serving as a lubricant will be described. Same reference numerals are denoted for the same configuring portions in each embodiment described above, and the description thereof will be appropriately omitted.

FIG. 13 is one part of a schematic cross-sectional view of the electric toothbrush according to the fourth embodiment of the present invention. In FIG. 13, the encircled figure is a view enlarging the vicinity of the bearing.

As described in the first embodiment, the bearing 400 is arranged near the distal end in the interior of the stem 110 configuring the vibration transmitting component 100. The distal end of the eccentric shaft configured by the shaft main body 306 and the eccentric member 307 (more specifically, distal end of the eccentric member 307) is supported in a freely rotating manner by the bearing 400.

A space region 115 is formed on the distal end side than the eccentric shaft at the distal end portion in the interior of the stem 110. Forming the space region 115 is the same in each embodiment described above as apparent from the figures referenced up to now.

In the present embodiment, a configuration of using the space region 115 as an oil reservoir for storing the lubricant oil O is adopted. In other words, the lubricant oil O is interposed as the lubricant at the slidably moving portion X of the eccentric shaft and the bearing 400.

However, the lubricant oil O gradually decreases through use over time. Thus, the quality lowers such as the slidable movement resistance gradually increases, the operation sound becomes louder, and the vibration increases. Accordingly, the lubricant oil is supplied to the slidably moving portion X as necessary by storing the lubricant oil O in the space region 115, as described above.

Therefore, the lubricant oil O can be interposed over a long period of time at the slidably moving portion X. The slidably moving state of the eccentric shaft and the bearing 400 thus can be stabilized over a long period of time. Therefore, the vibration state of each portion can be stabilized over a long period of time. Moreover, increase in the slidable movement resistance can be suppressed, the generation of abnormal noise (operation sound) can be suppressed, and increase in vibration can be suppressed. The current consumption can also be reduced.

In the present embodiment, the distal end 307a of the eccentric shaft projects out to the space region 115 side than the bearing 400. Thus, the vicinity of the front end 307a of the eccentric shaft is in a state of contacting the lubricant oil O. The lubricant oil O thus can be actively introduced (drawn) into the slidably moving portion X of the eccentric shaft and the bearing 400. Therefore, the lubricant oil O can be stably supplied to the slidably moving portion X.

The bearing 400 is arranged as a separate member near the distal end in the interior of the stem 110 to enhance abrasion resistance. That is, sufficient abrasion resistance may not be obtained with the raw material (e.g., POM) suited for the stem 110. Therefore, in the present embodiment, the bearing 400 using the raw material excelling in abrasion resistance is arranged. Oleoresin, oil retaining metal, or the like can be suitably applied for the raw material of the bearing 400. The concentricity can be easily enhanced by arranging the bearing 400 as a separate member.

FIGS. 14 to 18 show a fifth embodiment of the present invention. In the present embodiment, a configuration of further suppressing the transmission of vibration to the portion the user grips with hand when brushing teeth will be described. The configuration shown in the present embodiment is a configuration adopted in each embodiment above as illustrated in most of the figures referenced up to now, but will be more specifically described in the present embodiment. Same reference numerals are denoted for the same configuring portions as in each embodiment described up to now, and the description thereof will be appropriately omitted.

Figure 14:
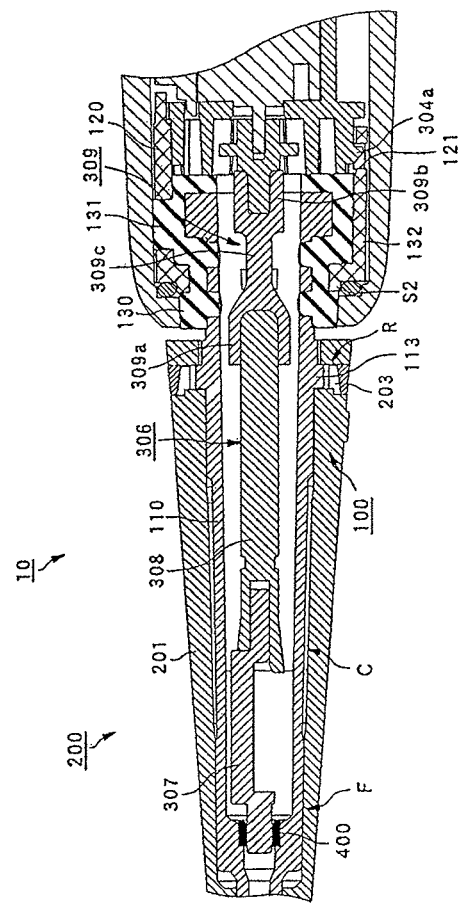
FIG. 14 is one part of a schematic cross-sectional view of an electric toothbrush according to a fifth embodiment of the present invention.
Figure 15:
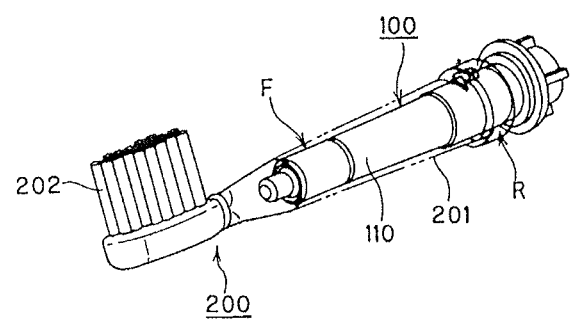
FIG. 15 is a partial perspective view of the vicinity of the brush component of the electric toothbrush according to the fifth embodiment of the present invention.
Figure 16:
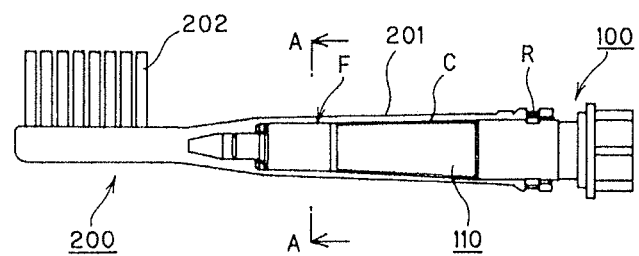
FIG. 16 is a partial perspective side view of the vicinity of the brush component of the electric toothbrush according to the fifth embodiment of the present invention.
Figure 17:
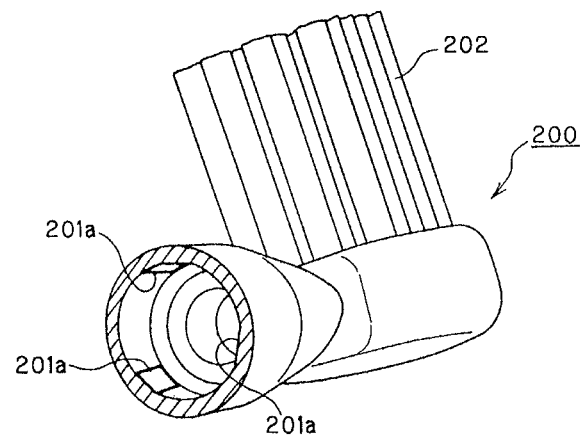
FIG. 17 is a partially cut perspective view of the brush component of the electric toothbrush according to the fifth embodiment of the present invention.
Figure 18:
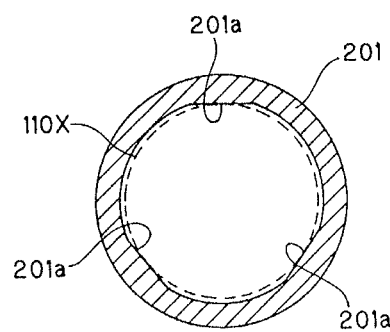
FIG. 18 is a view describing the contacting state of the brush component and the stem in the electric toothbrush according to the fifth embodiment of the present invention.

FIG. 14 is one part of a schematic cross-sectional view of the electric toothbrush according to the fifth embodiment of the present invention. FIG. 15 is a partial perspective view of the vicinity of the brush component of the electric toothbrush according to the fifth embodiment of the present invention. FIG. 16 is a partial perspective side view of the vicinity of the brush component of the electric toothbrush according to the fifth embodiment of the present invention. FIG. 17 is a partially cut perspective view of the brush component of the electric toothbrush according to the fifth embodiment of the present invention. The cut plane in FIG. 17 corresponds to the cross-section of AA in FIG. 16. FIG. 18 is a view describing the contacting state of the brush component and the stem in the electric toothbrush according to the fifth embodiment of the present invention. The cross-sectional view of the brush component in FIG. 18 corresponds to the cross-section of AA in FIG. 16.

As described in the first embodiment, the brush component 200 is attached to the vibration transmitting component 100 so as to cover the vibration transmitting component 100. As already described above, the brush component 200 includes the tubular portion 201 to be attached to the vibration transmitting component 100 and the brush portion 202 arranged at the distal end of the tubular portion 201. The brush component 200 is a consumable part, and is configured to be removable with respect to the vibration transmitting component 100 so as to be appropriately changed with a new one.

When the brush component 200 is attached to the vibration transmitting component 100, the vicinity of the front end F and the vicinity of the rear end R of the tubular portion 201 contact the stem 110, and a clearance C is formed between the inner wall surface of the tubular portion 201 and the outer wall surface of the stem 110 at the intermediate portion.

At the portion where the tubular portion 201 and the stem 110 contact, such contact is point contact (or line contact) at the plurality of locations with respect to the peripheral direction. It is, obviously, physically impossible to contact at a perfect point or line when referring to "point contact" or "line contact", and contact is made, in reality, at a surface of a very small area. Therefore, it is actually referring to contacting at as small as possible surface.

The contacting state will be more specifically described. FIGS. 17 and 18 show cross-sections of the tubular portion 201 in a region where the tubular portion 201 and the stem 110 contact at the vicinity of the front end F of the tubular portion 201.

In the present embodiment, a plane portion 201a is formed at three locations on the inner wall surface in the vicinity of the front end F of the tubular portion 201. Thus, the cross-sectional shape perpendicular to the axis at the inner wall surface of the tubular portion 201 is designed such that most of the portions are circular, but one part (three locations) of the circle is linear at the vicinity of the front end F.

The outer wall surface of the stem 110 is formed with a tapered surface such that the diameter becomes smaller towards the distal end, and the cross-sectional shape perpendicular to the axis is circular at all portions. 110X shown with a dotted line in FIG. 18 is the position of the surface of the outer wall surface of the stem 110.

According to the above configuration, the stem 110 contacts only the plane portion 201a at three locations on the inner wall surface of the tubular portion 201, as shown in FIG. 18, at the vicinity of the front end F of the tubular portion 201. Therefore, at the vicinity of the front end F of the tubular portion 201, the tubular portion 201 and the stem 110 point contact or line contact at three locations with respect to the peripheral direction.

At the vicinity of the rear end R of the tubular portion 201, the tubular portion 201 and the stem 110 are configured to point contact or line contact only at the portion of the L-shaped groove 203 arranged on the tubular portion 201 and the fit-in projection 113 arranged on the stem 110 described in the first embodiment. The L-shaped groove 203 and the fit-in projection 113 are respectively arranged at two locations with respect to the peripheral direction.

Therefore, at the vicinity of the rear end R of the tubular portion 201, the tubular portion 201 and the stem 110 point contact or line contact at two locations with respect to the peripheral direction.

According to the present embodiment, the location the vibration is directly transmitted from the vibration transmitting component 100 to the brush component 200 may be a limited portion (i.e., contacting portion), as described above. Therefore, the efficiency of the vibration transmission with respect to the brush portion 202 can be enhanced as much as possible, and the transmission of vibration to the portion the user grips with hand when brushing teeth can be suppressed.

In particular, in the present embodiment, the tubular portion 201 and the stem 110 contact the vicinity of the eccentric shaft bearing 400 (vicinity of the front end arranged with the brush portion 202), which is a factor that generates vibration. Thus, the vibration can be transmitted extremely efficiently with respect to the brush portion 202. The transmission of the vibration to the rear end side then can be suppressed, and the transmission of the vibration to the portion the user grips with hand when brushing teeth can be effectively suppressed.

The reason the efficiency of vibration transmission to the brush portion 202 can be enhanced by contacting the tubular portion 201 and the stem 110 only at two locations of the vicinity of the front end F and the vicinity of the rear end R, and forming the clearance C at the intermediate portion so that they do not contact will be described in further detail below.

Considering only the aspect of vibration transmission, the brush component 200 is ideally held by the vibration transmitting component 100 with the tubular portion 201 and the stem 110 contacted only at the vicinity of the eccentric member 307 (vicinity of the front end F) near the brush portion 202. However, if the contacting portion of the tubular portion 201 and the stem 110 is only at the vicinity of the front end F, the holding force of holding the brush component 200 is not sufficiently obtained, and the brush component 200 may detach from the vibration transmitting component 100 while the user is brushing teeth.

Therefore, the brush component 200 is held with the tubular portion 201 and the stem 110 contacted at two locations of the vicinity of the front end F and the vicinity of the rear end R, as described above. The brush component 200 thus does not detach during use, and the brush component 200 can be stably held by the vibration transmitting component 100.

If the tubular portion 201 and the stem 110 are contacted in a large area such as when the clearance C is eliminated, the vibration on the stem 110 side is transmitted to the entire tubular portion 201. The efficiency of the vibration transmission to the vicinity of the brush portion 202 thus lowers. The reason of contacting at two locations of the vicinity of the front end F and the vicinity of the rear end R is as described.

In the present embodiment, the shaft main body 306 of the eccentric shaft is configured by a first shaft member 308 connected to the eccentric member 307, and a second shaft member 309 connected to the side opposite to the eccentric member 307 with respect to the first shaft member 308 and having higher flexibility than the first shaft member 308.

The second shaft member 309 has a first fit-in portion 309a to be fitted with a distal end of the first shaft member 308 at one end, and a second fit-in portion 309b to be fitted with a distal end of a shaft on the motor side serving as a drive source on the other end.

A small diameter portion 309c smaller than the outer diameter of the first shaft member 308 is arranged between the first fit-in portion 309a and the second fit-in portion 309b. The material used for the first shaft member 308 may be the same material as for the eccentric member 307. For instance, the material may be a metal having high specific gravity such as brass or tungsten.

It may be configured with resin different from the eccentric member 307. For instance, a material that is not as hard as metal of high specific gravity such as polycarbonate (PC) is suitably used. Elastomer represented by TPE (thermoplastic elastomer) is suitable for the material of the second shaft member 309. When configuring the first shaft member 308 with resin and the second shaft member 307 with elastomer, they can be formed by integral molding while enhancing the manufacturing efficiency.

Therefore, the vibration can be absorbed by the second shaft member 309 by configuring the motor side of the shaft main body 306 configuring the eccentric shaft by the second shaft member 309 of high flexibility. Thus, the vibration at the portion of the second shaft member 309 can be absorbed in the process the vibration generated at the portion of the eccentric member 307 is transmitted to the rear end side through the eccentric shaft. Therefore, the transmission of the vibration to the side of the portion the user grips with hand when brushing teeth can be suppressed through the eccentric shaft from the eccentric member 307 side.

The transmission amount (vibration absorption amount) of the vibration can be adjusted (optimized) by adjusting the axial length and diameter of the small diameter portion 309c. Other effects such as below are obtained in addition to the vibration absorption effect by configuring part of the shaft main body 306 by the second shaft member 309 of high flexibility.

In other words, when using the electric toothbrush 10 according to the present embodiment, the user brushes teeth so as to press the distal end of the brush portion 202 against the teeth. Therefore, some users are assumed to press the brush portion 202 against the teeth with a force stronger than necessary. In this case, the eccentric shaft rotates in a bent state while involving vibration by eccentricity with a position (around an output shaft of the motor) distant from the acting point at where the force acts as a supporting point. Therefore, load is imposed on the bent portion (portion of the supporting point), and breakage easily occurs by degradation over time, which becomes the cause of shorter lifespan.

In the present embodiment, the portion close to the distal end of the shaft on the motor side of the eccentric shaft is configured by the second shaft member 309 of high flexibility, so that the portion of the second shaft member 309 (in particular, small diameter portion 309c) bends when the eccentric shaft bends. Thus, even if used in the bent state, degradation is less likely to occur over time (breakage is less likely to occur). The small diameter portion 309c is also the portion that can effectively absorb vibration.

As described above, the configuration in which the tubular portion 201 and the stem 110 are contacted only at the vicinity of the front end F and the vicinity of the rear end R and the clearance C is formed in the intermediate portion, and the configuration in which the shaft main body 306 of the eccentric shaft includes the first shaft member 308 and the second shaft member 309 having higher flexibility than the first shaft member 308 are also used in each embodiment described above.

The invention claimed is:

1. An electric toothbrush comprising:
   an eccentric shaft in which a center of gravity is arranged at a position shifted from a shaft center;
   an elongated vibration transmitting component having a first end portion which is closed and a second end portion which is opened, wherein the elongated vibration transmitting component houses the eccentric shaft;
   a bearing arranged inside the elongated vibration transmitting component and adjacent the first end portion, and supporting the eccentric shaft;
   an oil reservoir defined by the closed end portion of the vibration transmission component adjacent the bearing and storing a lubricant oil to be supplied to the bearing; and
   a brush component which includes a tubular portion having a closed end and an open end attached to the elongated vibration transmitting component, and a brush portion arranged at the closed end of the tubular portion, the tubular portion being configured to be detachably mounted on the elongated vibration transmitting component such that the elongated vibration transmitting component, where the eccentric shaft is housed, is inserted into the tubular portion;
   wherein a closed end portion of the tubular portion adjacent the closed end thereof and an open end portion of the tubular portion adjacent the open end thereof contact the first end portion and the second end portion of the elongated vibration transmitting component, respectively, with a middle portion of the tubular portion between the closed end portion and open end portion being spaced away from the elongated vibration transmitting component, defining a clearance between an inner wall surface of the tubular portion and an outer wall surface of the elongated vibration transmitting component, thereby transmitting vibration generated with the rotation of the eccentric shaft to the brush portion through a contact between the closed end portion and the first end portion and a contact between the open end portion and the second end portion when the tubular portion is mounted on the elongated vibration transmitting component.

2. The electric toothbrush according to claim 1, wherein the contact is accomplished by a plurality of point contacts or by a plurality of line contacts.

3. The electric toothbrush according to claim 2, wherein the point contacts are aligned in a peripheral direction.

4. The electric toothbrush according to claim 2, wherein the line contacts are aligned in a peripheral direction.

5. The electric toothbrush according to claim 1, wherein the elongated vibration transmitting component is formed with a projection on an outer surface at the second end portion thereof, and the tubular portion is formed with a groove on an inner surface at the open end portion thereof, whereby the projection engages the groove upon insertion of the elongated vibration transmitting component into the tubular portion.

6. The electric toothbrush according to claim 5, wherein the engagement between the projection and the groove is accomplished by a plurality of point contacts.

7. The electric toothbrush according to claim 5, wherein the engagement between the projection and the groove is accomplished by a plurality of the contacts.

* * * * *

UNITED STATES PATENT AND TRADEMARK OFFICE
CERTIFICATE OF CORRECTION

| | | |
|---|---|---|
| PATENT NO. | : 9,439,742 B2 | |
| APPLICATION NO. | : 14/315113 | |
| DATED | : September 13, 2016 | |
| INVENTOR(S) | : Jun Shimoyama | |

It is certified that error appears in the above-identified patent and that said Letters Patent is hereby corrected as shown below:

On the Title Page

In Column 1, Line 2 of (71) Applicant, delete "Kyoto-shi, Kyoto" and insert --Muko-shi--, therefor.

In the Specification

At Column 1, Line 7, delete "Jul. 9, 2007," and insert --Jul. 8, 2010,--, therefor.

At Column 14, Line 43, delete "bearing," and insert --bearing--, therefor.

Signed and Sealed this
Seventeenth Day of July, 2018

Andrei Iancu
*Director of the United States Patent and Trademark Office*